US006929778B2

United States Patent
Nunes et al.

(10) Patent No.: US 6,929,778 B2
(45) Date of Patent: Aug. 16, 2005

(54) SOLID PHASE MICROEXTRACTION FIELD KIT

(75) Inventors: Peter J. Nunes, Danville, CA (US); Brian D. Andresen, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 333 days.

(21) Appl. No.: 09/834,138

(22) Filed: Apr. 12, 2001

(65) Prior Publication Data

US 2002/0150504 A1 Oct. 17, 2002

(51) Int. Cl.[7] .......................... G01N 33/00; G01N 1/00
(52) U.S. Cl. .................... 422/61; 422/69; 422/100; 422/101; 436/174; 436/178; 436/808
(58) Field of Search ................. 422/61, 69, 99, 422/100, 101, 88; 436/174–178, 808

(56) References Cited

U.S. PATENT DOCUMENTS

| | | | | |
|---|---|---|---|---|
| 4,195,059 A | * | 3/1980 | Whitcher et al. | ............. 422/61 |
| 4,303,610 A | * | 12/1981 | Sardisco et al. | ............. 422/61 |
| 4,869,117 A | | 9/1989 | McAndless et al. | |
| 5,672,883 A | | 9/1997 | Reich | |
| 5,693,228 A | * | 12/1997 | Koehler et al. | ............. 210/656 |
| 5,983,661 A | | 11/1999 | Wiesman | |
| 6,042,787 A | * | 3/2000 | Pawliszyn | .................... 422/69 |
| 6,420,181 B1 | * | 7/2002 | Novak | ........................ 436/104 |

OTHER PUBLICATIONS

Optimization of the SPME Device Design For Field Applications, Fresenius' Journal of Analytical Chemistry, vol. 364, No. 7, Jul. 30, 1999, pp. 610–616, XP002224579, ISSN: 0937–0633.

* cited by examiner

Primary Examiner—Lyle A. Alexander
(74) Attorney, Agent, or Firm—James S. Tak; Alan H. Thompson; Eddie E. Scott

(57) ABSTRACT

A field kit for the collection, isolation and concentration of trace amounts of high explosives (HE), biological weapons (BW) and chemical weapons (CW) residues in air, soil, vegetation, swipe, and liquid samples. The field kit includes a number of Solid Phase Microextraction (SPME) fiber and syringe assemblies in a hermetically sealed transportation container or tubes which includes a sampling port, a number of extra SPME fiber and syringe assemblies, the fiber and syringe assemblies including a protective cap for the fiber, and an extractor for the protective cap, along with other items including spare parts, protective glove, and an instruction manual, all located in an airtight container.

17 Claims, 4 Drawing Sheets

SOLID PHASE MICROEXTRACTION FIELD KIT

The U.S. Government has rights in this invention pursuant to Contract No. W-7405-ENG48 between the U.S. Department of Energy and the University of California for the operation of Lawrence Livermore National Laboratory.

BACKGROUND OF THE INVENTION

The present invention relates to the collection end characterization of residues, particularly to a field kit which enables a consistent and reliable method for field analysis of various chemicals high explosives and chemical weapon related materials, and more particularly to a airtight, lightweight, field kit containing Solid Phase Microextraction (SPME) syringes in a hermetically sealed containers or tubes having sample ports therein, and equipment for enabling the use of SPME syringes.

Over the last decade extensive efforts have been carried out for development methods for characterization of various chemicals, particularly for the characterization of high explosives, chemical weapons, and biological weapons. These activities have centered on the collection, isolation, and concentration of trace amounts of these chemical residues in air, soil, vegetation, swipe, and liquid samples. Considerable resources have been applied to developing consistent and reliable methods for field analysis of high explosives and chemical weapons related materials.

Solid Phase Microextraction (SPME) is a widely recognized approach for the collection of various chemical residues, and SPME fibers and syringes are commercially available. SPME requires no solvents, is sensitive to low nanogram signature species, and can be repeatedly used in the field for the characterization of complex samples. A significant attribute of SPME fibers is their exceedingly high collection efficiencies. No chemical pretreatment or solvent extractions are necessary when using SPME fibers with GC or GC-MS instrumentation. However, there are some inherent problems with field SPME. SPME fibers tend to be very fragile and will break with the slightest impact. This makes transportation of SPME difficult in the field. Also, since SPME fibers are used for the sampling of potentially hazardous materials, the fibers need to be transported in a container that would prevent collected potentially lethal materials from contaminating the surroundings during transportation, as well as prevent cross contamination of different samples.

The field kit of the present invention provides a solution to the above-referenced problems and enables effect use of SPME for field analysis. The kit includes an air tight container in which is located a number of hermetically sealed individual transport containers or tubes within which are located SPME syringes, with the fiber of each syringe provided with a protective cap. The transport container or tubes each include a sampling port wherein material collected by one SPME fiber located within the transport container or tube can be transferred to another SPME fiber via the sampling port. The kit also contains a device for extracting and/or inserting the protective cap on the SPME fiber, as well as various spare parts, protective gloves and an instruction manual.

SUMMARY OF THE INVENTION

It is an object of the present invention to provide a field-deployable SPME kit.

A further object of the invention is to provide an SPME kit, small in size, that contains all necessary hardware for the proper collection and preservation of trace compounds in complicated samples.

Another object of the invention is to provide a field-deployable SPME kit which includes an assortment of SPME fibers hermetically sealed in their own transport tube to avoid any possibility of cross contamination.

Another object of the invention is to provide hermetically sealed transport containers for SPME syringes which include sample port, to enable sampling of the previously collected residue.

Another object of the invention is to provide a protective cap for the SPME fibers, and to provide a device for insertion and extraction of the protective cap over the fibers.

Another object of the invention is to provide an airtight SPME field kit which contains a number of SPME syringes within hermetically sealed transport containers, each syringe including a protective cap on the fiber or needle thereof, a device for extracting/inserting the protective cap, spare parts for the syringes and transport containers, protective gloves and an instruction manual.

Other objects and advantages of the present invention will become apparent from the following description and accompanying drawings. The present invention involves an SPME field kit for use in the collection, isolation, and concentration of trace amounts of high explosives (HE), chemical weapons (CW), biological warfare (BW) related materials, and other residues in air, soil, vegetation, swipe, and liquid samples, and particularly for field analysis of HE and CW-related materials. The field kit of this invention satisfies the needs for a field-deployable SPME kit that contains all necessary hardware for the proper collection and preservation of trace compounds in complicated samples. The SPME field kit includes an assortment of SPME syringes with fibers, all hermetically sealed in their own aluminum transport tube to avoid any possibility of damage to the fibers or cross contamination. The field kit is robust, supports chain-of-custody requirements, and provides the proper protocols for the safe collection of potentially lethal materials. In addition the field kit is small, lightweight, air tight and includes extra SPME fibers in a protective tube, protective gloves, extra parts for the transport tubes, and an instruction manual. The transport tubes include a sampling port which allows for sampling inside the transport tube using another SPME syringe without breaking the tube seals for quick test purposes. Protective caps are located over the SPME fibers, and the field kit includes a cap extractor/installer, thereby preventing damage to the fibers before and after use thereof.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1A:
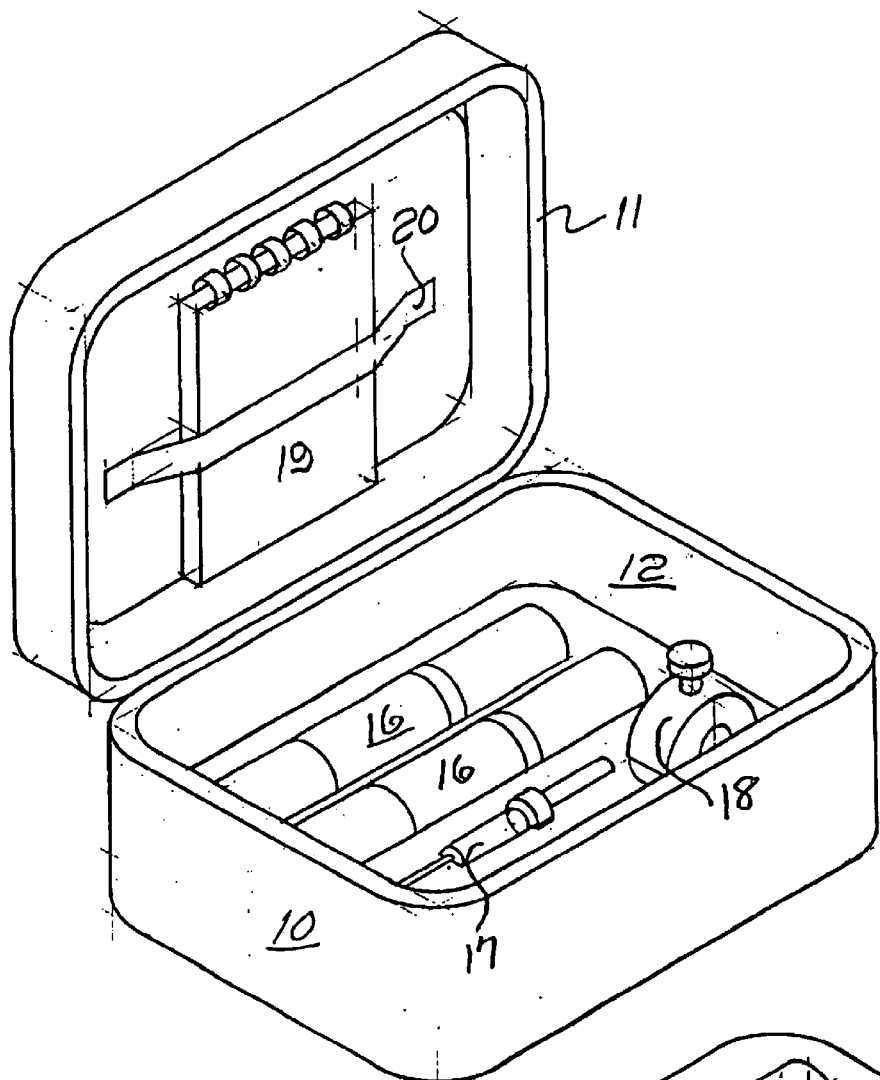
FIGS. 1A and 1B illustrate an embodiment of the field kit of the invention, with FIG. 1B illustrating a tray adapted to be removable, contained in the casing of FIG. 1A.

The present invention is directed to a Solid Phase Microextraction (SPME) field kit which is compact, light weight, air tight and contains all necessary equipment and an instruction manual for the collection, isolation, and concentration of trace amounts of HE, CW and BW related residues in air, soil, vegetation, swipe, and liquid samples. While SPME syringe and fiber assemblies are commercially available, the field kit includes a transport container or tube for the SPME assemblies as well as protective capping mechanisms for protection of the SPME fiber during transport, and a device for the extraction/installation of the protective caps, which are constructed of Teflon, for example. The transport container or tube includes a sampling port to enable sampling of the residue collected by the SPME fiber while retained within the transport container or tube. The SPME field kit of this invention is ideal for transport, collection of highly toxic and pathogenic samples, safe opening in the laboratory, and storage of important, highly toxic samples for exact characterization in the laboratory and in the field. The field kit enable the safe transport of SPME syringe/fiber assemblies for the safe collection and handling of highly toxic, unknown samples by first responders to the scene of a weapons of mass destruction (WMD) release.

The field kit of this invention, in addition to containing a number of transport tubes containing SPME syringe assemblies with protective fiber caps and the protective cap extractor/installer device, includes extra SPME fibers in protective tubes, extra seals for the transport tubes, Teflon caps, tamper proof sampling septums or seals, and an instruction manual.

The embodiment of the SPME field kit illustrated in the drawings and described hereinafter consist for major components mounted in a compact, light weight, air tight container or carrying case. First is an SPME fiber and syringe assembly, which is commercially available from Supleco, Bellefonte, Pa., and is a volatile organic collector. Second, is a SPME transport tube or container, which has internal dimensions which precisely fit the Supleco fiber and syringe assembly for protection thereof and prevents cross contamination of samples, and is, for example, composed of a hermetically sealed aluminum which has been anodized to help prevent corrosion of the aluminum. The transport tube uses two Viton, for example. O-rings that keep an air tight seal within the tube and a pin locking mechanism to prevent leakage. The transport tube also includes a sampling port at one end to allow sampling inside the transport tube using another SPME fiber and syringe assembly without breaking the tube seals, to enable test sampling of potentially toxic chemicals collected by the SPME syringe located within the transport tube. This quick test will determine if the exterior of the SPME fiber syringe assembly was contaminated during the sampling process. The sampling port utilizes a chemical resistant Teflon faced septum, for example, which can be easily replaced when necessary. Third, is a SPME fiber or needle cap extractor/installer. This device safely removes and applies a protective Teflon cap, for example, that attaches to the SPME fiber or needle. Fourth, is support equipment, which includes extra SPME fibers in a protective tube, protective gloves, extra Viton O-rings, Teflon caps, Teflon faced septums, and an instruction manual. In the embodiment illustrated the field kit contains five transport tubes containing SPME fiber and syringe assemblies within a casing or container that is compact, lightweight, and airtight. Thus, the field kit enables one to collect, transport, and test various residues for field or laboratory analysis. The field kit is robust, supports chain-of-custody requirements, and provides the proper protocols for the safe collection of potentially lethal materials, and has particular application for first responders at WMD incidents.

Figure 1B:
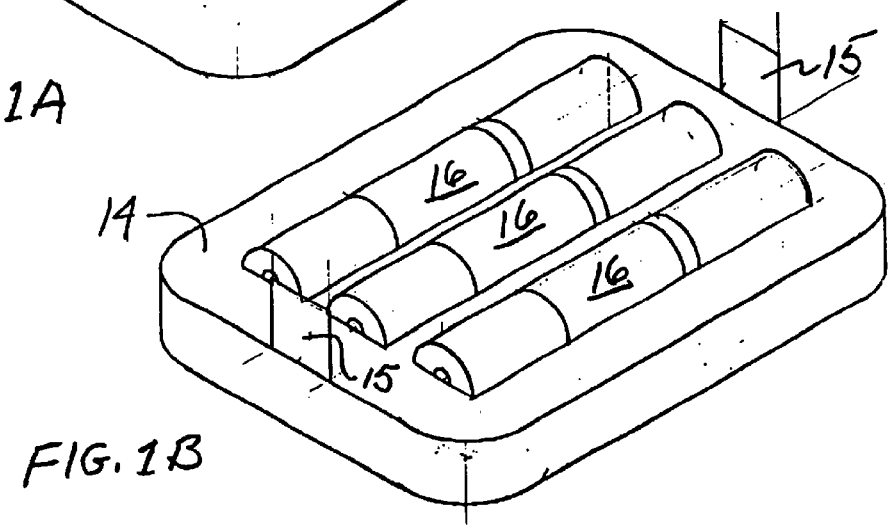
Figure 2:
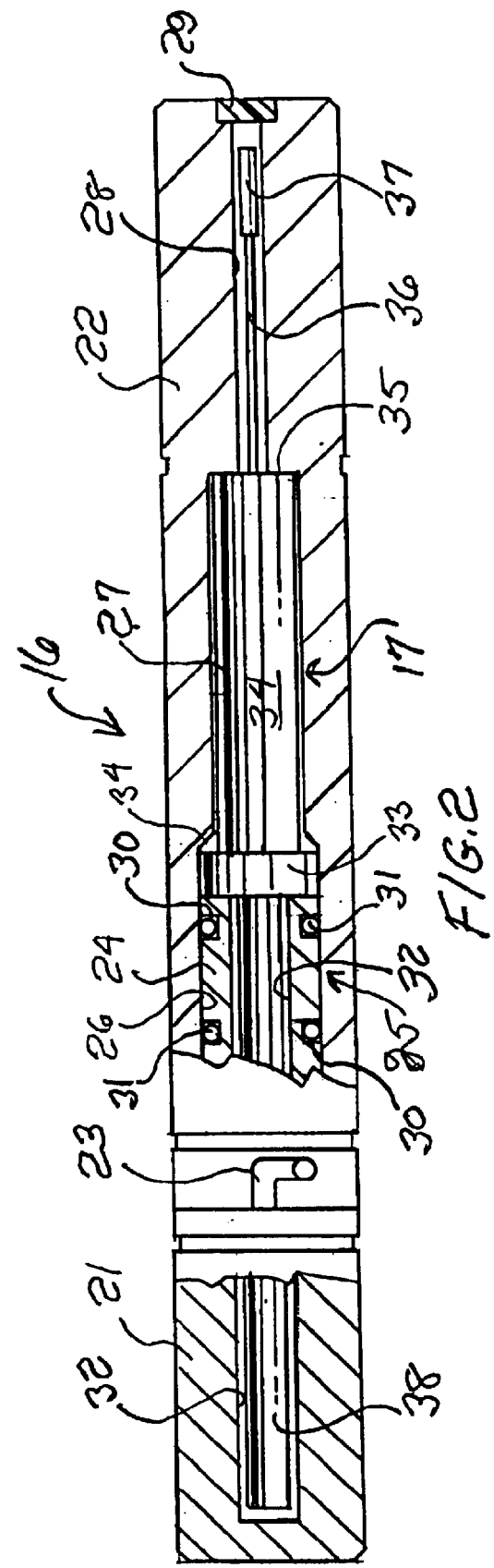
FIG. 2 is a cross-section view of an embodiment of a transport tube of FIGS. 1A–1B with an SPME fiber and syringe assembly secured therein.
Figure 3:
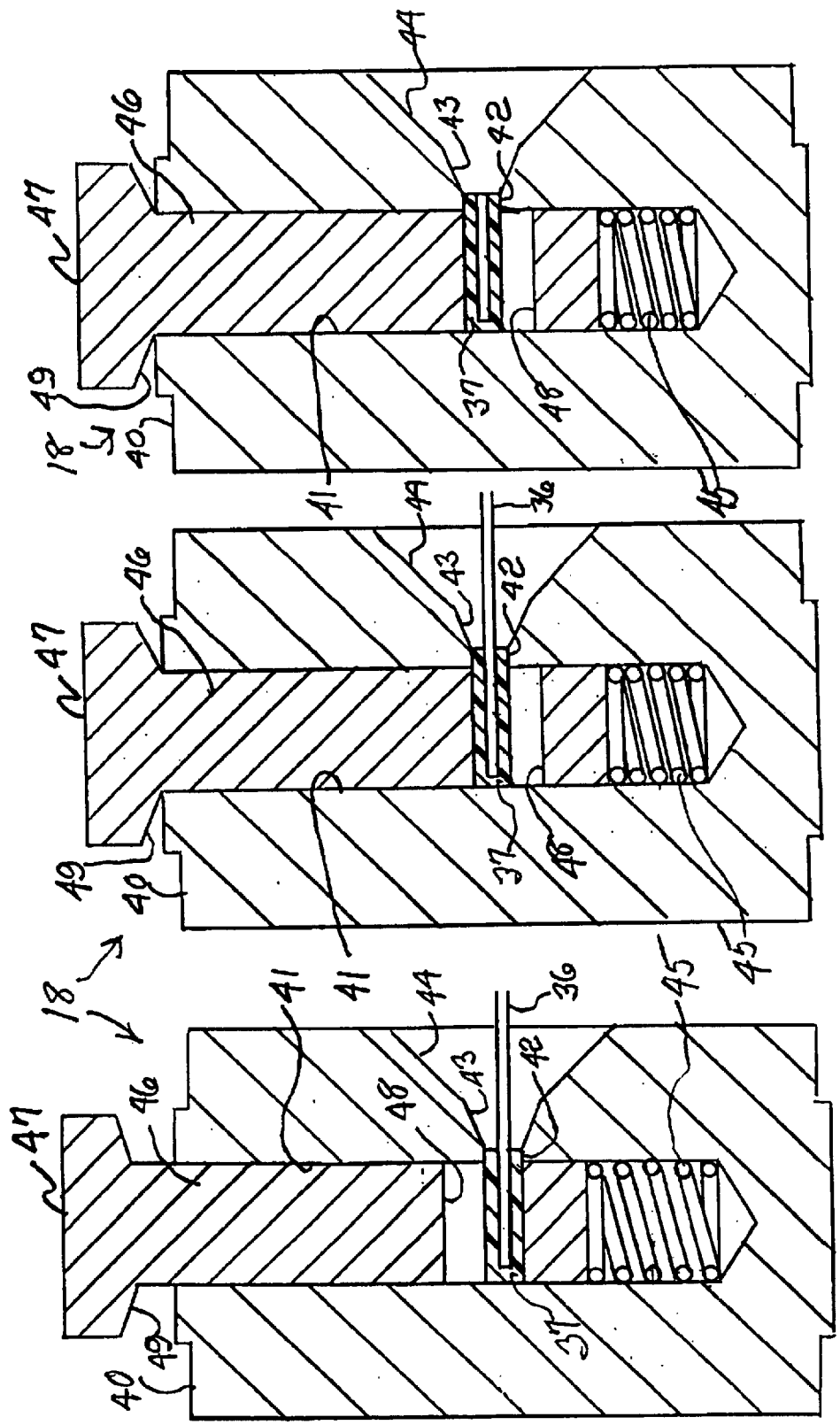
FIGS. 3A–3C illustrate the operational sequence of the extractor for the removal of the protective cap of the SPME fiber.

Referring now to an embodiment of the field kits, as illustrated in the drawings, with FIGS. 1A and 1B showing a casing, housing or kits having a removable tray shown in FIG. 1B, made in accordance with the present invention. The casing in FIG. 1A includes a body section 10 and a hinged cover or lid section 11 having one the top thereof, not shown, a carrying handle assembly. The body and lid section are constructed to provide an air tight interior 12 within which a tray 14 (FIG. 1B) having tabs 15 is positioned during transport and removed by tabs 15 from interior 12 for use. The tray 14 contains three (3) transport tubes 16, described in detail hereinafter with respect to FIG. 2, while the body section of the casing contains, as shown, contains two transport tubes 16, a spare SPME fiber/syringe assembly 17, in a protective cover, and an extractor tool 18 for removing a protective cap from the SPME fiber as shown in FIGS. 3A–3C. While not shown, the casing body section 10 also contains extra parts, such as a fiber protective cap, Viton O-rings for the transport tubes, seals or septums for the sampling port of the transport tubes, and protective gloves. The lid section 11 of the casing contains an instruction manual 19 secured by a removable strap 20.

The transport tubes 16 each comprises two housing sections 21 and 22 constructed of anodized aluminum, for example to help prevent corrosion thereof, with sections 21 and 22 being interconnected by a pair of twist and lock mechanism 23, only one shown, and with section 21 having a reduced diameter end 24 which extends into a opening generally indicated at 25 in section 22 and which includes three different diameter sections 26, 27 and 28, with opening section 28 being closed by a seal or septum 29 and forms a sampling port as described hereinafter. Reduced diameter end 24 of housing section 21 is provided with annular grooves 30 in which O-rings 31, constructed of Viton, are located to provide a hermetic seal with the surface of opening section 26 of housing section 22. Housing section 22 also includes an opening 32 which extends through reduced diameter end 24. The opening sections 26, 27 and 28 of housing section 22 and opening 32 in housing section 21 are designed and configured to securely retain therein an SPME fiber/syringe assembly 17. Note that end section 24 of housing section 21 is constructed to abut a flange 33 on assembly 17 so as to retain the flange against a tapered section 34 of opening 25 located intermediate opening sections 26 and 27, and with a body section 34 of assembly 17 abutting a surface 35 intermediate opening sections 27 and 28, such that the needle or fiber 36 of assembly 17 having a protective cap 37 extends freely into opening section 28 in housing section 22, and a plunger section 38 of assembly 17 extends freely into opening 32 in housing section 21. Thus, the SPME fiber/syringe assembly 17 is securely retained within transport tube 16. Each transport tube 16 of FIGS. 1A–1B retains an SPME fiber/syringe assembly 17. It should be noted that the fiber or needle of each assembly 17 might be constructed to collect the same or different residue, as discussed above.

FIGS. 3A–3C illustrate cross-sections and operations of extractor tool 18 which comprises a housing 40 having an opening 41 extending partially there-through and an opening 42 in the side of housing 40 which communicates with opening 41. Opening 42 includes two tapered sections 43 and 44. Located in opening 41 is a spring 45 and a plunger or member 46 having a head 47 and a opening or groove 48 which aligns with opening 42 when plunger 46 is moved. In operation of the extractor tool, a fiber 36 of syringe assembly 17 having a protective cap 37 (see FIG. 2), having been removed from a transport tube 16, is inserted through opening 42 of housing 40 and into opening or groove 48 of plunger 46, as shown in FIG. 3A. Inward movement of plunger 46 against spring 45 retains the protective cap 37 in tool 18, as shown in FIG. 3B. Note that the head 47 of plunger 46 is configured with a tapered surface 49 to abut housing 40 so as to prevent further inward movement of the plunger 46 which could result in damage to the protective cap 37 and fiber 36. Upon removal of the fiber 36 for use thereof from protective cap 37, the cap is retained in tool 18, as shown in FIG. 3C. After use of the fiber 36 it is reinserted into protective cap 37 being retained in tool 18, where after the plunger is raised, which allows the removal of cap 37 and fiber 36 from openings 48 and 42, where after the fiber/syringe assembly 17 is again positioned in a transport tube 16, as seen in FIG. 2, by securing housing section 21 in housing section 22 via the twist and lock mechanism 23.

Figure 4:
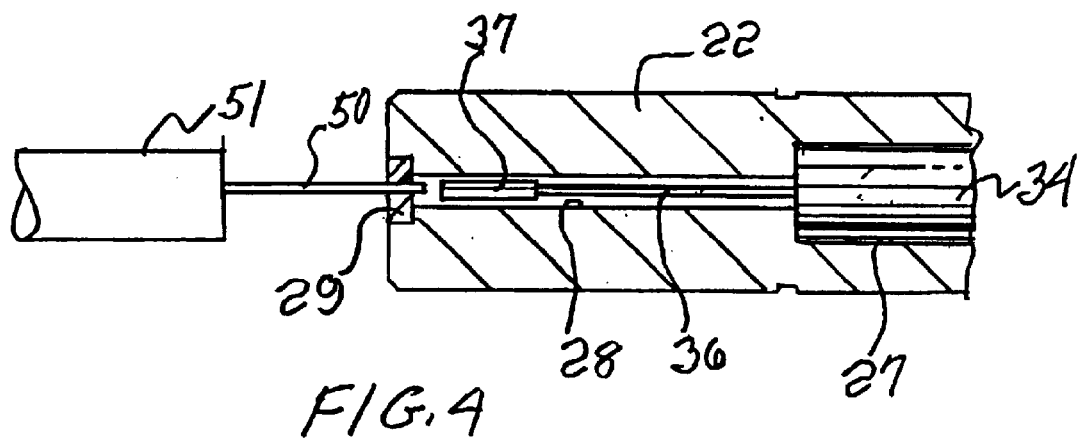
FIG. 4 is a cross-section of an end of the transport tube of FIG. 2 showing testing of a contained SPME fiber by another SPME fiber via a sampling port.

After a fiber 36 of syringe assembly 17 has been exposed to some residue, etc., it is secured in transport tube 16. To prevent possible contamination by the exposed fiber located in transport tube 16, the septum 29, which may be a chemical resistant Teflon-faced seal, permits sampling of the environment within transport tube 16, as shown in FIG. 4. To carry out sampling of the environment within transport tube 16, another fiber/syringe assembly, similar to assembly 17 is utilized and the fiber/syringe assembly. Similar to assembly 17 is utilized and the fiber or needle 50 of syringe 51 is inserted through septum 29 in the end of transport tube 16 and into opening section 28 containing the exposed fiber 36.

It has thus been shown that the present invention provides a field-deployable SPME kit that contains all necessary hardware and operation manual for the proper collection and preservation of trace compounds in complicated samples. The SPME kit includes transport tubes for SPME fiber/syringe assemblies which securely retains the assemblies therein, while including a sample port by which the environment within the transport tube can be safely tested, and in addition the SPME fiber is provided with a protective cap, and the kit includes a cap extractor tool. In addition, the kit contains replacement parts for the transport tubes, extra fiber/syringe assemblies, and protective gloves, the extra fiber/syringe assemblies being contained in a protective cover such as a plastic wrap or plastic seal.

While an embodiment of the kit and embodiments of the transport tubes have been illustrated and described to exemplify and explain the principles of the invention, such are not intended to be limiting. Modifications and changes may become apparent to those skilled in the art and it is intended that the invention be limited only by the scope of the appended claims.

What is claimed is:

1. A field-deployable solid phase microextraction kit comprising:
   a casing having a lid section; a plurality of solid phase microextraction (SPME) fiber/syringe assemblies; and at least a plurality of hermetically sealed transport tubes located in said casing,
   each transport tube for sealably and securely retaining one of said SPME fiber/syringe assemblies and preventing cross-contamination with another one of said SPME fiber/syringe assemblies retained in another transport tube when carried together in said casing,
   wherein each of said transport tubes includes means located at an end of said transport tube for allowing sampling of an environment within said transport tube, to determine contamination of a retained SPME fiber/syringe assembly.

2. The kit of claim 1,
   additionally include at least spare parts for said transport of tubes, at least one spare SPME fiber/syringe assembly, protective gloves and an instruction manual.

3. The kit of claim 1,
   wherein said casing and said lid section are constructed so as to form an airtight interior.

4. The kit of claim 1,
   wherein said transport tubes are constructed of anodized aluminum.

5. The kit of claim 1,
   additionally including a tray containing a plurality of transport tubes removably positioned in said casing.

6. The kit of claim 1,
   wherein said means located at an end of said transport tube for allowing sampling comprises a septum mounted in one end through which the interior of the transport tube may be tested.

7. The kit of claim 1,
   wherein each of said SPME fiber/syringe assemblies includes a fiber protective cap.

8. The kit of claim 1,
   additionally including a fiber protective cap extraction tool.

9. The kit of claim 1,
   wherein said transport tubes are composed of two interconnected sections constructed to be hermetically sealed, each of said two sections having openings therein constructed to secure one of said SPME fiber/syringe assemblies therein.

10. The kit of claim 9,
    additionally including at least one seal in said two interconnected sections.

11. A field-deployable solid phase microextraction kit comprising:
    a casing having a lid section; a plurality of solid phase microextraction (SPME) fiber/syringe assemblies; and at least a plurality of hermetically sealed transport tubes located in said casing,
    each transport tube for sealably and securely retaining one of said SPME fiber/syringe assemblies and preventing cross-contamination with another one of said SPME fiber/syringe assemblies retained in another transport tube when carried together in said casing,
    said transport tubes being composed of two interconnected sections constructed to be hermetically sealed, each of said two sections having openings therein constructed to secure one of said SPME fiber/syringe assemblies therein, said two interconnected sections of said transport tubes being secured together by a twist/lock arrangement,
    and wherein each of said transport tubes includes a septum mounted in one end through which the interior of the transport tube may be tested.

12. A field-deployable solid phase microextraction kit comprising:
    a casing having a lid section, a plurality of solid phase microextraction (SPME) fiber/syringe assemblies each having a fiber protective cap; a tool for removing and inserting said fiber protective caps on said SPME fiber/syringe assemblies; and at least a plurality of hermetically sealed transport tubes located in said casing, each transport tube for sealably and securely retaining one of said SPME fiber/syringe assemblies and preventing cross-contamination with another one of said SPME fiber/syringe assemblies retained in another transport tube when carried together in said casing, said transport tubes being composed of two interconnected sections constructed to be hermetically sealed, each of said two sections having openings therein constructed to secure one of said SPME fiber/syringe assemblies therein, and at least one seal in said two interconnected sections, one of said two interconnected sections including an end section which extends into the other of said two interconnected sections, and wherein said seal comprises a pair of spaced O-ring mounted in its end section and constructed to contact an internal surface of said other said two interconnected sections.

13. The kit of claim 12, wherein said tool comprises a housing having a spring mounted plunger therein, said plunger having an opening therein, and said housing having an opening constructed to align with said opening in said plunger, whereby a protective cap is retained in said openings in said housing and said plunger by movement of said plunger, is released from being retained in said housing and said plunger by movement of said plunger.

14. In a SPME kit having at least one solid chase microextraction (SPME) fiber/syringe assembly, the improvement comprising:

at least one hermetically sealed transport tube for a SPME fiber/syringe assembly, said transport tube having a configured interior corresponding to an exterior of the SPME fiber/syringe assembly, whereby said assembly is secured within said transport tube; and said transport tube including a seal in one end through which an interior of said transport tube could be tested to determine contamination of the SPME fiber syringe assembly when retained in said transport tube.

15. The improvement of claim 14, wherein said at Least one transport tube includes two interconnected sections, means for securing said two sections together, and a sealing arrangement located intermediate said two interconnected sections.

16. The improvement of claim 14, additionally including a protective cap for the fiber of said SPME fiber/syringe assembly.

17. The improvement of claim 16, additionally including a tool for removing said protective cap from said fiber and reinstalling said protective cap on said fiber.

* * * * *